(12) United States Patent
Frangioni

(10) Patent No.: US 9,326,666 B2
(45) Date of Patent: May 3, 2016

(54) MULTI-CHANNEL MEDICAL IMAGING SYSTEM

(71) Applicant: Beth Israel Deaconess Medical Center, Boston, MA (US)

(72) Inventor: John V. Frangioni, Wayland, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 277 days.

(21) Appl. No.: 14/082,899

(22) Filed: Nov. 18, 2013

(65) Prior Publication Data

US 2014/0073885 A1   Mar. 13, 2014

Related U.S. Application Data

(60) Division of application No. 12/307,204, filed as application No. PCT/US2007/072803 on Jul. 3, 2007, now Pat. No. 8,620,410, which is a continuation-in-part of application No. 10/507,253, filed as application No. PCT/US03/07596 on Mar. 11, 2003, now Pat. No. 8,229,548.

(60) Provisional application No. 60/818,365, filed on Jul. 3, 2006, provisional application No. 60/363,413, filed on Mar. 12, 2002.

(51) Int. Cl.
| | |
|---|---|
| *A61B 1/04* | (2006.01) |
| *A61B 1/00* | (2006.01) |
| *A61B 1/06* | (2006.01) |
| *A61B 5/00* | (2006.01) |
| *B82Y 5/00* | (2011.01) |
| *B82Y 10/00* | (2011.01) |
| *A61B 1/313* | (2006.01) |
| *A61B 5/026* | (2006.01) |
| *A61B 19/00* | (2006.01) |
| *A61K 49/00* | (2006.01) |

(52) U.S. Cl.
CPC ............... *A61B 1/043* (2013.01); *A61B 1/0005* (2013.01); *A61B 1/00186* (2013.01); *A61B 1/0638* (2013.01); *A61B 1/0684* (2013.01); *A61B 1/3132* (2013.01); *A61B 5/0071* (2013.01); *A61B 5/0086* (2013.01); *A61B 5/0261* (2013.01); *A61B 19/5212* (2013.01); *A61K 49/006* (2013.01); *B82Y 5/00* (2013.01); *B82Y 10/00* (2013.01)

(58) Field of Classification Search
CPC ..................................................... A61B 5/0071
See application file for complete search history.

(56) References Cited

U.S. PATENT DOCUMENTS 6,293,911 B1 *   9/2001   Imaizumi ........... A61B 1/00009
                                                                600/160

* cited by examiner

*Primary Examiner* — Peter Luong
(74) *Attorney, Agent, or Firm* — Parker Ibrahim & Berg LLC; Stephen D. LeBarron

(57) ABSTRACT

A medical imaging system provides simultaneous rendering of visible light and fluorescent images. The system may employ dyes in a small-molecule form that remain in a subject's blood stream for several minutes, allowing real-time imaging of the subject's circulatory system superimposed upon a conventional, visible light image of the subject. The system may provide an excitation light source to excite the fluorescent substance and a visible light source for general illumination within the same optical guide used to capture images. The system may be configured for use in open surgical procedures by providing an operating area that is closed to ambient light. The systems described herein provide two or more diagnostic imaging channels for capture of multiple, concurrent diagnostic images and may be used where a visible light image may be usefully supplemented by two or more images that are independently marked for functional interest.

6 Claims, 6 Drawing Sheets

Fig. 5

MULTI-CHANNEL MEDICAL IMAGING SYSTEM

RELATED APPLICATIONS

This application is a divisional application of U.S. Ser. No. 12/307,204, filed Oct. 22, 2009, now allowed, which is a national phase filing under 35 U.S.C. §371 of published International Application No. PCT/US07/072803, filed on Jul. 3, 2007, which is incorporated herein by reference in its entirety. International Application PCT/US07/72803 was published in English as Publication No. WO 2008/042486. International Application PCT/US07/72803 claims priority to U.S. Prov. App. No. 60/818,365, filed on Jul. 3, 2006, the entire content of which is incorporated herein by reference. This application is also a continuation-in-part of U.S. patent application Ser. No. 10/507,253, filed on Sep. 10, 2004, incorporated herein by reference in its entirety. U.S. application Ser. No. 10/507,253 was filed as a U.S. national phase filing of International App. No. PCT/US03/07596, filed on Mar. 11, 2003, which claims priority to U.S. Prov. App. No. 60/363,413, filed on Mar. 12, 2002. The benefit of the foregoing applications is claimed herein to the extent permitted by law.

GOVERNMENT INTERESTS

The United States Government has certain rights in this invention pursuant to National Institute of Health Grant # R21CA88245 and Department of Energy Grant # DE-FG02-01ER63188.

BACKGROUND OF THE INVENTION

The invention is directed to a medical imaging system, and more particularly to a medical imaging system capable of acquiring and displaying two or more diagnostic images at two different wavelengths along with a color image of an anatomical site in the visible wavelength range.

Absorption and fluorescent dyes, such as indocyanine green, have proven useful for medical imaging applications. Some of the more commonly used dyes share a number of useful characteristics. First, the dyes are suitable for labeling antibodies or low-molecular-weight ligands of diagnostic significance, or otherwise adapted for sequestration or preferential uptake at a site of interest such as a lesion. The dyes are safe for injection or other introduction into a live subject. And finally, the dyes emit light at a specific wavelength when excited, so that their location and concentration may be tracked.

A number of imaging systems have been devised to detect and display these dyes within living tissue. For example, dyes such as indocyanine green have been used to visualize blood flow in eyes. In some cases, such as U.S. Pat. No. 6,293,911 to Imaizumi et al., a dye imaging device has been combined with a visible light imaging system. Imaizumi describes endoscopic tools that generate images of dye-labeled antibodies superimposed over visible light images captured from within the body. As a significant disadvantage, the Imaizumi system employs a number of separate cavities within an endoscopic tool for light sources and image capture, thus requiring a greater cross-sectional area for the endoscope. As a further disadvantage, the Imaizumi patent only discloses endoscopic applications, and may not be suitable for use in open surgical applications where ambient light may extend into the excitation and/or emission wavelengths of the dye.

There remains a need for improved surgical and diagnostic imaging tools capable of generating circulatory blood flow images or other functional images along with visible light images of a subject.

SUMMARY OF THE INVENTION

A medical imaging system provides simultaneous rendering of visible light and fluorescent images. The system may employ dyes in a small-molecule form that remains in a subject's blood stream for several minutes, allowing real-time imaging of the subject's circulatory system superimposed upon a conventional, visible light image of the subject. The system may also employ dyes or other fluorescent substances associated with antibodies, antibody fragments, or ligands that accumulate within a region of diagnostic significance. In one embodiment, the system provides an excitation light source to excite the fluorescent substance and a visible light source for general illumination within the same optical guide that is used to capture images. In another embodiment, the system is configured for use in open surgical procedures by providing an operating area that is closed to ambient light. The systems described herein usefully provide two or more diagnostic imaging channels for capture of multiple, concurrent diagnostic images. The systems described herein may be used in imaging applications where a visible light image may be usefully supplemented by two or more images that are independently marked for functional interest.

The medical imaging system may include a visible light source providing light over a range of wavelengths that includes one or more wavelengths of visible light, an excitation light source providing light at one or more wavelengths outside the range of wavelengths of the visible light source, the one or more wavelengths selected to excite a fluorescent substance, which emits one or more photons at an emission wavelength; an electronic imaging device; an optical guide having a first end with a lens that captures an image of a subject and a second end that couples the image to the electronic imaging device; and a filter for coupling the visible light source and the excitation light source into the optical guide, the filter reflecting some of the light provided by the visible light source and some of the light from the excitation light source toward the subject, the filter further transmitting some visible light from the subject captured by the lens toward the electronic imaging device, and the filter further transmitting the emission wavelength from the subject captured by the lens toward the electronic imaging device.

In another embodiment, the system may include a visible light source illuminating a subject, the visible light source providing a range of wavelengths including one or more wavelengths of visible light; an excitation light source illuminating the subject, the excitation light source providing an excitation wavelength that is not one of the one or more wavelengths of visible light; a fluorescent substance introduced into a circulatory system of the subject, the fluorescent substance being soluble in blood carried by the circulatory system and the fluorescent substance emitting photons at an emission wavelength in response to the excitation wavelength; an electronic imaging device that captures an image of a field of view that includes some portion of the subject and the circulatory system of the subject, the image including a first image obtained from the one or more wavelengths of visible light and a second image obtained from the emission wavelength; and a display that renders the first image and the second image, the second image being displayed at a visible light wavelength.

In another embodiment, the system may include an operating area closed to ambient light, the operating area including a surgical field where a surgical procedure may be performed on a subject; a visible light source illuminating the surgical field, the visible light source providing a range of wavelengths including one or more wavelengths of visible light; an excitation light source illuminating the surgical field, the excitation light source including at least one wavelength outside the range of wavelengths of visible light; a fluorescent substance suitable for in vivo use, the fluorescent substance fluorescing at an emission wavelength in response to the at least one wavelength of the excitation light source, the fluorescent substance being introduced into the surgical field; an electronic imaging device that captures a visible light image of the surgical field and an emission wavelength image of the surgical field; and a display that renders the visible light image and the emission wavelength image of the surgical field, the emission wavelength image being displayed at a visible light wavelength.

In another embodiment, the system may include a visible light source that illuminates a subject, the visible light source providing a range of wavelengths including one or more wavelengths of visible light; an excitation light source that illuminates the subject at the same time that the visible light source illuminates the subject, the excitation light source providing an excitation wavelength that is not one of the one or more wavelengths of visible light; a fluorescent substance introduced into a circulatory system of the subject, the fluorescent substance being soluble in blood carried by the circulatory system and the fluorescent substance emitting photons at an emission wavelength in response to the excitation wavelength; and an electronic imaging device that captures an image of a field of view that includes some portion of the subject and the circulatory system of the subject, the image including a first image obtained from the one or more wavelengths of visible light and a second image concurrently obtained from the emission wavelength.

In another aspect, the embodiments described above may include a first optical channel for a first diagnostic image having a first wavelength, a second optical channel for a second diagnostic image having a second wavelength, and a third optical channel for a visible light image.

BRIEF DESCRIPTION OF DRAWINGS

The invention will be appreciated more fully from the following further description thereof, with reference to the accompanying drawings, wherein.

DETAILED DESCRIPTION OF CERTAIN
EMBODIMENTS OF THE INVENTION

To provide an overall understanding of the invention, certain illustrative embodiments will now be described, including a system for generating superimposed circulatory and tissue images in video format. However, it will be understood that the methods and systems described herein can be suitably adapted to other medical imaging applications where visible light tissue images may be usefully displayed with diagnostic image information obtained from outside the visible light range and superimposed onto the visible light image. More generally, the methods and systems described herein may be adapted to any imaging application where a visible light image may be usefully displayed with a superimposed image captured from areas within the visible light image that are functionally marked to emit photons outside the visible light range by a dye or other material. For example, the systems and methods are applicable to a wide range of diagnostic or surgical applications where a target pathology, tissue type, or cell may be labeled with a fluorescent dye or other fluorescent substance. These and other applications of the systems described herein are intended to fall within the scope of the invention.

Figure 1:
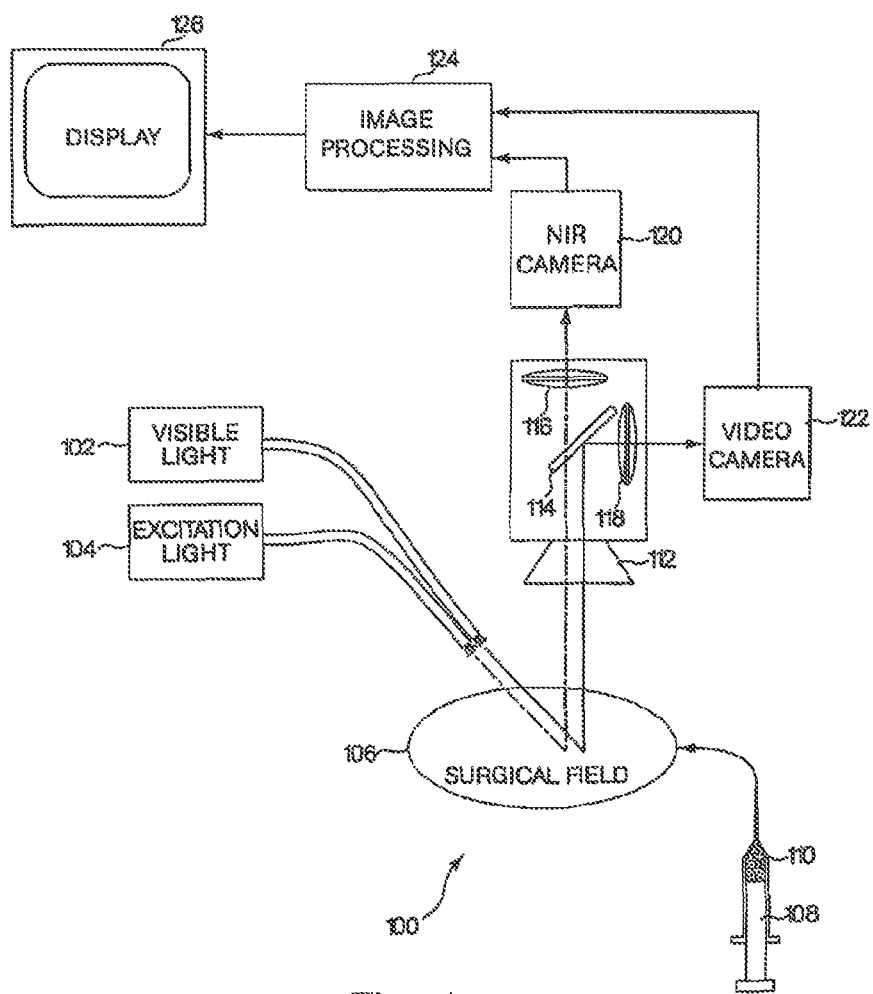
FIG. 1 shows an embodiment of an imaging system for use during open surgery.

FIG. 1 shows an embodiment of an imaging system for use during open surgery. The imaging system 100 may include a visible light source 102, and excitation light source 104, a surgical field 106, a dye source 108 containing a dye 110, a lens 112, a first filter 114, a second filter 116, a third filter 118, a near-infrared camera 120, a video camera 122, an image processing unit 124, and a display 126. In general, the visible light source 102 and the excitation light source 104 illuminate the surgical field 106. The dye 110 may be introduced from the dye source 108, such as through injection into the bloodstream of a subject. An image from the surgical field 106 is then captured by two cameras, the video camera 122 capturing a conventional, visible light image of the surgical field 106 and the near-infrared camera 120 capturing a diagnostic image based upon the distribution of the dye 110 in the surgical field 106. These images may be combined by the image processing unit 124 and presented on a display 126 where they may be used, for example, by a surgeon conducting a surgical procedure. Each aspect of the system 100 is now described in more detail.

The imaging system 100 may be surrounded by an operating area (not shown) closed to ambient light. As will become clear from the following, many visible light sources such as incandescent lamps, halogen lamps, or daylight may include a broad spectrum of electromagnetic radiation that extends beyond the range of visible light detected by the human eye and into wavelengths used in the present system as a separate optical channel for generating diagnostic images. In order to effectively detect emission in these super-visible light wavelengths, it is preferred to enclose the surgical field 106, light sources 102, 104, and cameras 120, 122 in an area that is not exposed to broadband light sources. This may be achieved by using an operating room closed to external light sources, or by using a hood or other enclosure or covering for the surgical field 106 that prevents invasion by unwanted spectrum. The visible light source 102 may then serve as a light source for the visible light camera 122, and also for provide conventional lighting within the visible light spectrum. As used herein, the term "operating area" is intended specifically to refer to an open surgical site that is closed to ambient light. Endoscopic or laparoscopic applications, as described below, are confined to surgical procedures within a closed body cavity, and do not include an operating area as that term is intended herein.

The visible light source 102 may be, for example, a near-infrared depleted white light source. This may be a one-hundred fifty Watt halogen lamp with one or more fitters to deplete wavelengths greater than 700 nanometers ("nm"). Generally, any light source constrained to wavelengths between 400 nm and 700 nm may operate as the visible light source 102. In certain applications, the excitation light source 104 and resulting emission from the dye 110 may have wavelengths near or below 700 nm, as with Cy5 dye, which emits light when excited at 650 nm. These near-red dyes may be used with the present system, however, this requires a visible light source 102 that excludes a portion of the visible light spectrum in which the dye operates, i.e., a far-red depleted white light source. Similarly, applications using quantum dots as a fluorescent substance may have absorption or emission wavelengths anywhere in the visible light spectrum, and a suitable visible light source should be depleted at the wavelength(s) of interest. As such, the visible light source 102 should more generally be understood to be a source of light that includes some, but not necessarily all, of the wavelengths of visible light.

It should also be understood that, in a far-red imaging system or infrared imaging system such as those noted above, the near-infrared camera 120 described in the example embodiment will instead be a camera sensitive to the emission wavelength of the dye 110 or other fluorescent substance, and that other modifications to light sources, filters and other optics will be appropriate. Similar modifications may be made to isolate a band of wavelengths for dye excitation and emission anywhere within or outside the visible light range, provided that suitable optics, cameras, and dyes are available. Other fluorescent substances may also be used. For example, quantum dots may emit at visible light wavelengths, far-red, near-infrared, and infrared wavelengths, and at other wavelengths, typically in response to absorption below their emission wavelength. Suitable adjustments will be made to the excitation light source 104 and the emission camera, the near-infrared camera 120 in the example embodiment, for such applications. Cameras sensitive to far-red, near-infrared, and infrared wavelengths are commercially available.

The excitation light source 104 provides light at a wavelength that excites the dye 110. This may be, for example, a laser diode such as a 771 nm, 250 mW laser diode system, which may be obtained from Laser Components of Santa Rosa, Calif. Other single wavelength, narrowband, or broadband light sources may be used, provided they do not interfere with the visible light image captured by the video camera 122 or the emission wavelength of the dye 110. The near-infrared band is generally understood to include wavelengths between 700 nm and 1000 nm, and is a useful wavelength range for a number of readily available excitation light sources 104 and dyes 110 that may be used with the systems described herein. Suitable optical coupling and lenses may be provided to direct each of the visible light source 102 and the excitation light source 104 at an area of interest within the surgical field 106.

The surgical field 106 may be any area of a subject or patient that is open for a surgical procedure. This may be, for example, an open chest during a procedure such as a revascularization or cardiac gene therapy, where visualization of the circulatory system may improve identification of areas at risk for myocardial infarction. Blood flow visualization may permit an assessment of coronary arteries during a coronary artery bypass graft, or an assessment of blood flow and viability during introduction of genes for endothelial growth factor or fibroblast growth factor to induce neovascularization within ischemic regions of the heart. More generally, the surgical field 106 may include any areas of a patient's body, such as a region of the body that includes a tumor that is to be surgically removed, and that is amenable to visualization with fluorescent dyes, such as through the use of labeled antibodies.

The dye source 108 may be any instrument used for injection or other introduction of the dye 110 into a subject, such as a hypodermic needle or angiocath. Where, for example, the dye 110 is highly soluble in blood, the dye source 108 may be administered anywhere on the subject, and need not be near the surgical field 106. For example, it has been found that IRDye78-CA (the carboxylic acid form of IRDye78), when injected intravenously into a live laboratory rat, produced peak vasculature image strength of an open heart approximately 5-10 seconds after injection, and remained adequate for visualization for over one minute. In certain embodiments, the dye source 108 may not use injection. For example, the dye source 108 may spray or otherwise apply the dye 110 to an area of interest, Depending upon the type of dye and the imaging technique, the dye 110 may be delivered in a discrete dose, or may be continuously or intermittently applied and re-applied by the dye source 108.

The dye 110 may be any dye suitable for use in vivo and having excitation and emission wavelengths suitable for other components of the system 100. Typically, the dye 110 will be diluted to 25-50 µM for intravenous injection, such as with phosphate buffered saline, which may be supplemented with Cremophor EL (Sigma) and/or absolute ethanol. A number of suitable near-infrared dyes are described below.

'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The terms 'amine' and 'amino' are art-recognized and refer to both unsubstituted and substituted amines as well as ammonium salts, e.g., as can be represented by the general formula:

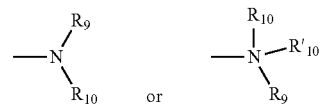

wherein R9, R10, and R'10 each independently represent hydrogen or a hydrocarbon substituent, or R9 and R10 taken together with the N atom to which they are attached complete a heterocycle having from 4 to 8 atoms in the ring structure. In preferred embodiments, none of R9, R10, and R'10 is acyl, e.g., R9, R10, and R'10 are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., R'10 is present) are referred to as 'ammonium' groups. In amino groups other than ammonium groups, the amine is preferably basic, e.g., its conjugate acid has a pKa above 7.

The terms 'amido' and 'amide' are art-recognized as an amino-substituted carbonyl, such as a moiety that can be represented by the general formula:

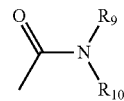

wherein R9 and R10 are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heteroeyelyl, and heteroaryl.

The terms 'alkertyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group, Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocylic aliphatic, or —O-heterocyclic aliphatic.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring, Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Cycloalkyl ring' refers to a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 4 to about 10 carbon atoms, preferably from 4 to 7 carbon atoms, and most preferably from 5 to 6 carbon atoms in the ring. Bicyclic cycloalkyl rings contain from 8 to 12 carbon atoms, preferably from 9 to 10 carbon atoms in the ring, Cycloalkyl rings may be unsubstituted or substituted with from 1 to 4 substituents on the ring. Preferred cycloalkyl ring substituents include halo, cyano, alkyl, heteroalkyl, haloalkyl, phenyl, phenoxy or any combination thereof. More preferred substituents include halo and haloalkyl. Preferred cycloalkyl rings include cyclopentyl, cyclohexyl, cyclohex-enyl, cycloheptyl, and cyclooctyl. More preferred cycloalkyl rings include cyclohexyl, cycloheptyl, and cyclooctyl.

The term 'carbonyl' is art-recognized and includes such moieties as can be represented by the general formula:

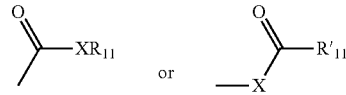

wherein X is a bond or represents an oxygen or a sulfur, and R11 represents a hydrogen, hydrocarbon substituent, or a pharmaceutically acceptable salt, R11' represents a hydrogen or hydrocarbon substituent. Where X is an oxygen and R11 or R11' is not hydrogen, the formula represents an 'ester'. Where X is an oxygen, and R11 is as defined above, the moiety is referred to herein as a carboxyl group, and particularly when R11 is a hydrogen, the formula represents a 'carboxylic acid'. Where X is an oxygen, and R11' is hydrogen, the formula represents a 'formate'. In general, where the oxygen atom of the above formula is replaced by sulfur, the formula represents a 'thiocarbonyl' group. Where X is a sulfur and $R_{11}$ or R11' is not hydrogen, the formula represents a 'thioester.' Where X is a sulfur and R11 is hydrogen, the formula represents a 'thiocarboxylic acid.' Where X is a sulfur and R11' is hydrogen, the formula represents a 'thioformate.' On the other hand, where X is a bond, R11 is not hydrogen, and the carbonyl is bound to a hydrocarbon, the above formula represents a 'ketone' group. Where X is a bond, R11 is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms, C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, atylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl, Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is noon-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring, Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine; oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes apart of the chain or ring. For example, in cresol, six carbon atoms are member atoms of the ring and the oxygen atom and the carbon atom of the methyl substituent are not member atoms of the ring.

As used herein, the term 'nitro' means —NO2.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'sulfate' is art-recognized and includes a moiety that can be represented by the general formula:

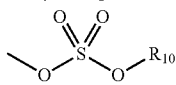

in which R10 is as defined above.

A 'substitution' or 'substituent' on a small organic molecule generally refers to a position on a multivalent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkenyl, and heteroalkynyl, heteroaralkyl, aralkyl, aryl or heteroaryl. It will be understood by those skilled in the art that certain substituents, such as aryl, heteroaryl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and non-aromatic organic compounds which can be substituted or unsubstituted.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

In certain embodiments, the subject method employs a fluorescent dye having a structure of the formula:

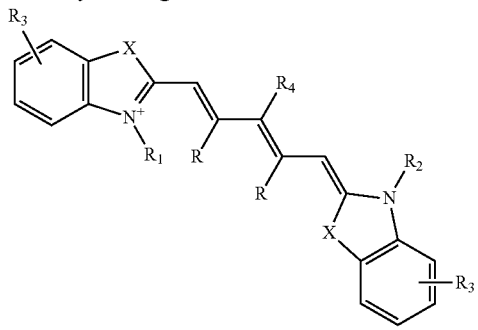

wherein, as valence and stability permit:

X represents ((R)2, S, Se, O, or NR5;

R represents H or lower alkyl, or two occurrences of R, taken together, form a ring together with the carbon atoms through which they are connected;

R1 and R2 represent, independently, substituted or unsubstituted lower alkyl, lower alkenyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof;

R3 represents, independently for each occurrence, one or more substituents to the ring to which it is attached, such as a fused ring (e.g., a benzo ring), sulfate, phosphate, sulfonate, phosphonate, halogen, lower alkyl, hydroxyl, amino, cyano, nitro, carboxylic acid, amide, etc., or a pharmaceutically acceptable salt thereof;

R4 represents H, halogen, or a substituted or unsubstituted ether or thioether of phenol or thiophenol; and R5 represents, independently for each occurrence, substituted or unsubstituted lower alkyl, cycloalkyl, cycloalkylalkyl, aryl, or aralkyl, e.g., optionally substituted by sulfate, phosphate, sulfonate, phosphonate, halogen, hydroxyl, amino, cyano, nitro, carboxylic acid, amide, etc., or a pharmaceutically acceptable salt thereof.

Dyes representative of this formula include indocyanine green, as well as:

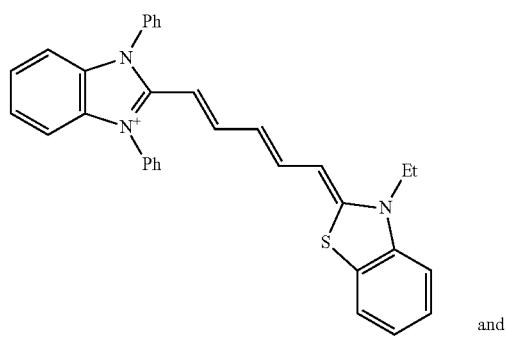

and

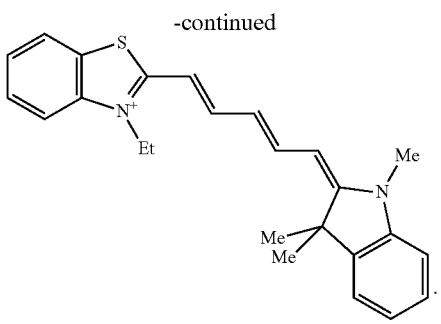

In certain embodiments wherein two occurrences of R taken together form a ring, the ring is six-membered, e.g., the fluorescent dye has a structure of formula:

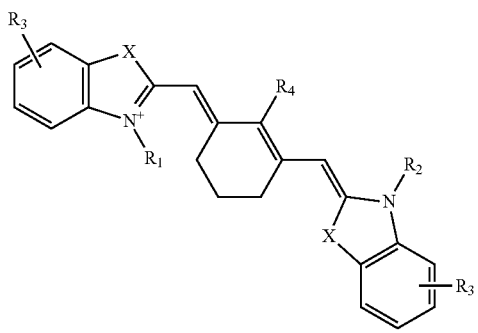

wherein X, R1, R2, R3, R4, and R5 represent substituents as described above.

Dyes representative of this formula include IRDye78, IRDye80, IRDye38, IRDye40, IRDye41, IRDye700, IRDye800, Cy7 (AP Biotech), and compounds formed by conjugating a second molecule to any such dye, e.g., a protein or nucleic acid conjugated to IRDye800, IRDye40, or Cy7, etc. The IRDyes are commercially available from Li-Cor Biosciences of Lincoln, Nebr., and each dye has a specified peak absorption wavelength (also referred to herein as the excitation wavelength) and peak emission wavelength that may be used to select suitable optical hardware for use therewith. It will be appreciated that other dyes may also be used, including the far-red dyes noted above, provided suitable adjustments are made to the visible light imaging components of the system 100, and other near-infrared dyes or infrared substances such as the previously mentioned quantum dots. Several specific dyes suited for specific imaging techniques are now described.

IRDye78-CA is useful for imaging the vasculature of the tissues and organs. The dye in its small molecule form is soluble in blood, and has an in vivo early half-life of several minutes. This permits multiple injections during a single procedure. Indocyanine green has similar characteristics, but is somewhat less soluble in blood and has a shorter half-life, IRDye78 may also be used in other imaging applications, since it can be conjugated to tumor-specific ligands for tumor visualization. More generally, IRDye78 may be linked to an antibody, antibody fragment, or ligand associated with a tumor. Presence of the tumor or lesion may then be visualized using the techniques described above.

As another example, IR-786 partitions efficiently into mitochondria and/or endoplasmic reticulum in a concentration-dependent manner, thus permitting blood flow and ischemia visualization in a living heart. The dye has been successfully applied, for example, to image blood flow in the heart of a living laboratory rat after a thoracotomy. More generally, IR-786 may be used for non-radioactive imaging of areas of ischemia in the living heart, or other visualization of the viability of other tissues.

While a number of suitable dyes have been described, it should be appreciated that such fluorescent dyes are examples only, and that more generally, any fluorescent substance may be used with the imaging systems described herein, provided the substance has an emission wavelength that does not interfere with visible light imaging. This includes the fluorescent dyes described above, as well as substances such as quantum dots which may have emission wavelengths above 1000 nm, and may be associated with an antibody, antibody fragment, or ligand and imaged in vivo. All such substances are referred to herein as fluorescent substances, and it will be understood that suitable modifications may be made to components of the imaging system for use with any such fluorescent substance.

The lens 112 may be any lens suitable for receiving light from the surgical field 106 and focusing the light for image capture by the near-infrared camera 120 and the video camera 122. The lens 112 may include one or more optical coatings suitable for the wavelengths to be imaged, and may provide for manual, electronically-assisted manual, or automatic control of zoom and focus.

The first filter 114 may be positioned in the image path from the lens 112 such that a visible light image having one or more visible light wavelengths is directed toward the video camera 122, either by reflection or transmittance. An emission image from the excited dye 110 passes through the lens 112 and is directed toward the near infrared camera 120, again either through reflection or transmittance. A number of arrangements of the cameras 120, 122 and the first filter 114 are possible, and may involving reflecting or transmitting either the visible light image or the emission wavelength image.

In one embodiment, IRDye78-CA (carboxylic acid) having a peak absorption near 771 nm and a peak emission near 806 nm, is used with the system 100. In this embodiment, the first filter 114 may be a 785 nm dichroic mirror that transmits near-infrared light and reflects visible light. The first filter 114 may be positioned within an image path from the lens 112 such that a visible light image of the surgical field 106 is reflected toward the video camera 122 through the third filter 118. The third filter 118 may be, for example, a 400 nm-700 nm light filter. At the same time, the first filter 114 is positioned with the image path from the lens 112 such that a near-infrared image (i.e., the excitation wavelength image) is transmitted toward the near-infrared camera 120 through the second filter 116. The second filter 116 may be an 810 nm+/− 20 nm near-infrared emission filter. The filters may be standard or custom-ordered optical components, which are commercially available from optical component suppliers, Other arrangements of filters and other optical components may be used with the system 100 described herein.

The near-infrared camera 120 may be any still or moving image camera suitable for capturing images at the emission wavelength of the excited dye 110. The near-infrared camera may be, for example, an Orca-ER near-infrared camera with settings of gain 7, 2×2 binning, 640×480 pixel field of view, and an exposure time of 20 msec and an effective frame rate of fifteen frames per second. The Orca-ER is commercially available from Hamamatsu Photonic Systems of Bridgewater, N.J. It will be understood that the near-infrared camera 120 of FIG. 1 is only an example. An infrared camera, a far-red camera, or some other camera or video device may be used to capture an emission wavelength image, with the camera and any associated filters selected according to the wavelength of a corresponding fluorescent substance used with the imaging system. As used herein, the term "emission wavelength camera" is intended to refer to any such camera that may be used with the systems described herein.

The video camera 122 may be any video camera suitable for capturing images of the surgical field 106 in the visible light spectrum. In one embodiment, the video camera 122 is a color video camera model HV-D27, commercially available from Hitachi of Tarrytown, N.Y. The video camera 122 may capture red-green-blue (RGB) images at thirty frames per second at a resolution of 640×480 pixels. More generally, the near-infrared camera 120 and the video camera 122 may be any device capable of photonic detection and conversion to electronic images, including linear photodiode arrays, charge coupled device arrays, scanning photomultiplier tubes, and so forth.

The display 126 may be a television, high-definition television, computer monitor, or other display configured to receive and render signals from the image processing unit 124. The surgical field 106 may also be a neurosurgical site, with a surgical microscope used to view the surgical field 106. In this embodiment, the display 126 may be a monocular or binocular eyepiece of the surgical microscope, with the near-infrared image superimposed on the visible light image in the eyepiece. In another embodiment, the eyepiece may use direct optical coupling of the surgical field 106 to the eyepiece for conventional microscopic viewing, with the near-infrared image projected onto the eyepiece using, for example, heads-up display technology.

The image processing unit 124 may include any software and/or hardware suitable for receiving images from the cameras 120, 122, processing the images as desired, and transmitting the images to the display 126. In one embodiment, the image processing unit 124 is realized in software on a Macintosh computer equipped with a Digi-16 Snapper frame grabber for the Orca-ER, commercially available from DataCell of North Billerica, Massachussets, and equipped with a CG-7 frame grabber thr the HV-D27, commercially available from Scion of Frederick Md., and using IPLab software, commercially available from Sanalytics of Fairfax, Va. While a Macintosh may be used in one embodiment, any general purpose computer may be programmed to perform the image processing functions described herein, including an Intel processor-based computer, or a computer using hardware from Sun Microsystems, Silicon Graphics, or any other microprocessor manufacturer.

Generally, the image processing unit 124 should be capable of digital filtering, gain adjustment, color balancing, and any other conventional image processing functions. The image from the near-infrared camera 120 is also typically shifted into the visible light range for display at some prominent wavelength, e.g., a color distinct from the visible light colors of the surgical field 106, so that a superimposed image will clearly depict the dye. The image processing unit 124 may also perform image processing to combine the image from the near-infrared camera 120 and the video camera 122. Where the images are displayed side-by-side, this may simply entail rendering the images in suitable locations on a computer screen. Where the images are superimposed, a frame rate adjustment may be required. That is, if the video camera 122 is capturing images at the conventional rate of thirty frames per second and the near-infrared camera 120 is taking still pictures with an effective frame rate of fifteen frames per second, some additional processing may be required to render the superimposed images concurrently. This may entail either reducing the frame rate of the video camera 122 to the frame rate of the near-infrared camera 120 either by using every other frame of video data or averaging or otherwise interpolating video data to a slower frame rate. This may instead entail increasing the frame rate of the near-infrared image data, either by holding each frame of near-infrared data over successive frames of video data or extrapolating near-infrared data, such as by warping the near-infrared image according to changes in the video image or employing other known image processing techniques.

Generally, any combination of software or hardware may be used in the image processing unit 124. The functions of the image processing unit 124 may be realized, for example, in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The functions may also, or instead, include one or more application specific integrated circuits, programmable gate arrays, programmable array logic devices, or any other device or devices that may be configured to process electronic signals. Any combination of the above circuits and components, whether packaged discretely, as a chip, as a chipset, or as a die, may be suitably adapted to use with the systems described herein.

It will further be appreciated that each function of the image processing unit 124 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The image processing unit 124 may be deployed using software technologies or development environments including a mix of software languages, such as Java, C++, Oracle databases, SQL, and so forth. It will be further appreciated that the functions of the image processing unit 124 may be realized in hardware, software, or some combination of these.

In one embodiment, the visible light source 102 is a near-infrared depleted visible light source, the excitation light source 104 is a 771 nm, 250 mW laser diode, the dye 110 is indocyanine green or IRDye78-CA, the first filter 114 is a 785 nm dichroic mirror configured to transmit near-infrared light and reflect visible light, the second filter 116 is an 810 nm+/− 20 nm near-infrared emission filter, and the third filter 118 is a 400 nm to 700 nm filter. The image processing unit 124 is a computer with software for image capture from the near-infrared camera 120 and the video camera 122, for making suitable color adjustment to the images from the near-infrared camera 120, for making frame rate adjustments to the video camera 122 image, and for combining the two images for superimposed display on the display 126.

The systems described above have numerous surgical applications. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies.

Figure 2:
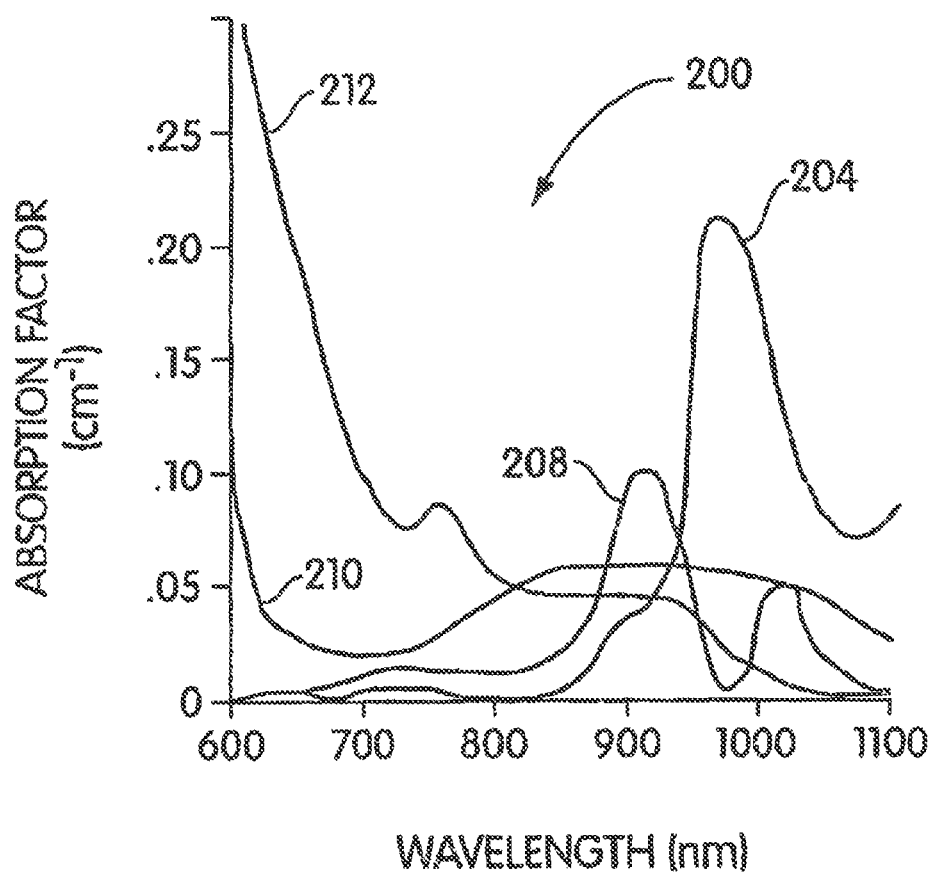
FIG. 2 shows a near-infrared window used by the imaging system.

FIG. 2 shows a near-infrared window used by the imaging system. The near-infrared window 200 is characterized by wavelengths where absorbance is at a minimum. The components of living tissue with significant near-infrared absorbance include water 204, lipid 208, oxygenated hemoglobin 210, and deoxygenated hemoglobin 212. As shown in FIG. 2, oxygenated hemoglobin 210 and deoxygenated hemoglobin have significant absorbance below 700 nm. By contrast, lipids 208 and water 204 have significant absorbance above 900 nm. Between 700 nm and 900 nm, these absorbances reach a cumulative minimum referred to as the near-infrared window 200. While use of excitation and emission wavelengths outside the near-infrared window 200 is possible, as described in some of the examples above, fluorescence imaging within the near-infrared window 200 offers several advantages including low tissue autofluorescence, minimized tissue scatter, and relatively deep penetration depths. While the near-infrared window 200 is one useful wavelength range for imaging, the systems described herein are not limited to either excitation or emission wavelengths in this window, and may employ, for example, far-red light wavelengths below the near-infrared window 200, or infrared light wavelengths above the near-infrared window 200, both of which may be captured using commercially available imaging equipment.

Figure 3:
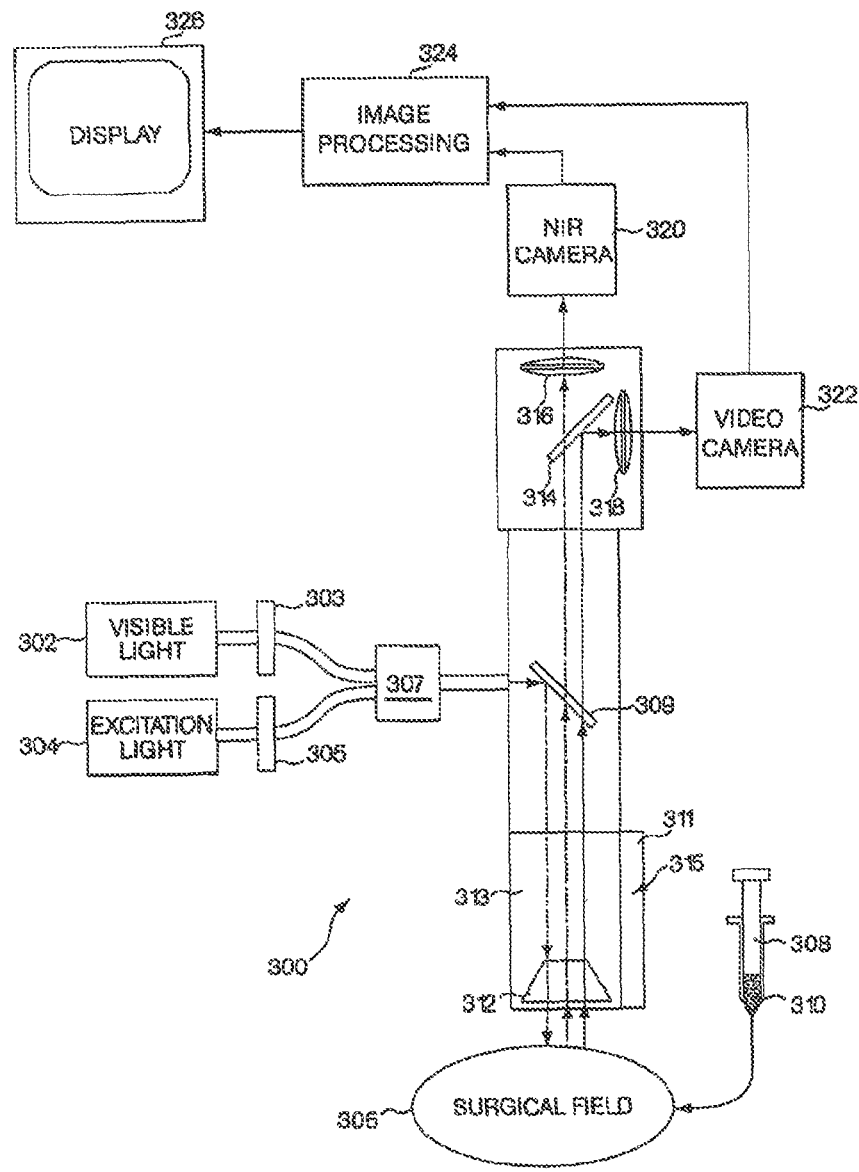
FIG. 3 shows an embodiment of an imaging system for use in an endoscopic tool.

FIG. 3 shows an embodiment of an imaging system for use in an endoscopic tool. The imaging system 300 may include a visible light source 302, and excitation light source 304, a surgical field 306, a dye source 308 containing a dye 310, a lens 312, a first filter 314, a second filter 316, a third filter 318, a near-infrared camera 320, a video camera 322, an image processing unit 324, and a display 326. In general, the visible light source 302 and the excitation light source 304 illuminate the surgical field 306. The dye 310 may be introduced from the dye source 308, such as through injection into the bloodstream of a subject. An image from the surgical field 306 is then captured by two cameras, the video camera 322 capturing a conventional, visible light image of the surgical field 306 and the near-infrared camera 320 capturing a diagnostic image based upon the distribution of the dye 310 in the surgical field 306. These images may be combined by the image processing unit 324 and presented on a display 326 where they may be used, for example, by a surgeon conducting a surgical procedure. In general, each of these components may be any of those components similarly described with reference to FIG. 1 above. Differences for an endoscopic tool are now described.

The imaging system 300 for use as an endoscopic tool may further include a first lens/collimator 303 for the visible light source, a second lens/collimator 305 for the excitation light source 304, an optical coupler 307 that combines the excitation light and the visible light, a dichroic mirror 309, and an endoscope 311 having a first cavity 313 and a second cavity 315.

The first lens/collimator 303, the second lens/collimator 305, and the optical coupler 307 serve to combine the excitation light and the visible light into a single light source. This light source is coupled into the first cavity 313 through the dichroic mirror 309. In one embodiment, the dichroic mirror 309 preferably provides fifty percent reflection of light having wavelengths from 400 nm to 700 nm, in order to optimize an intensity of visible light that reaches the video camera 322 after illuminating the surgical field 306 and passing through the dichroic mirror 309 on its return path to the video camera 322. The dichroic mirror 309 also preferably has greater than ninety percent reflection of wavelength from the excitation light source 304, such as between 700 nm and 785 nm, so that these wavelengths are not transmitted to the cameras 320, 322 after reflecting off the surgical field. Using this arrangement, visible and excitation light sources 302, 304 share the first cavity 313 of the endoscope with the return light path for a visible light image and an emission wavelength image.

The second cavity 315 of the endoscope 311 may be provided for insertion of a tool, such as an optical tool like a laser for irradiation of a site in the surgical field 306, or a physical tool like an instrument for taking a biopsy of tissue within the surgical field. By combining the optical paths of the imaging system 300 within a single cavity of the endoscope 311, the combined gauge of the first cavity 313 for imaging and the second cavity 315 may be advantageously reduced.

The imaging system 300 may instead be used with a laparoscope. Typically, a laparoscope is inserted into a body cavity through an incision, as distinguished from an endoscope which is inserted through an existing body opening such as the throat or rectum. A laparoscope has a different form factor than an endoscope, including different dimensional requirements. Furthermore, use of a laparoscope involves at least one additional step of making an incision into a body so that the laparoscope may be inserted into a body cavity. The laparoscope may be used with any of the imaging systems described above, and the imaging system 300 of FIG. 3 in particular would provide the benefit of a narrower bore for illumination and imaging optics, It will further be appreciated that the imaging system 300 may be used to simplify imaging devices other than endoscopes and laparoscopes, such as by providing an integrated, coaxial illumination and image capture device using the techniques described above.

In addition to the surgical applications noted above in reference to FIG. 1, the endoscopic tool of FIG. 3 may be used for direct visualization of malignant or pre-malignant areas within a body cavity, or for image-guided placement of gene therapy and other medicinals to an area of interest within the body cavity.

Figure 4:
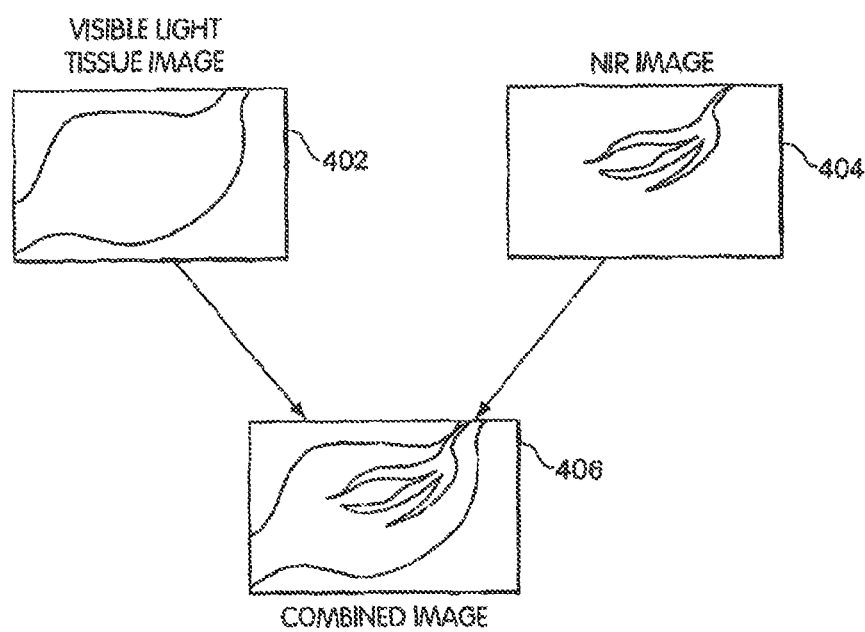
FIG. 4 shows an image displaying both a circulatory system and surrounding tissue.

FIG. 4 shows an image displaying both a circulatory system and surrounding tissue. As described above, a visible light tissue image 402 is captured of tissue within a surgical field. As noted above, the visible light tissue image 402 may include a subset of visible light wavelengths when an optical channel for dye imaging includes a wavelength within the visible light range. A near-infrared image 404 is also captured of the same (or an overlapping) field of view of the surgical field. Although referred to here for convenience as a near-infrared image, it should be clear that the dye-based image 404 may also, or instead, employ other wavelengths, such as far-red or infrared wavelengths. The near-infrared image 404 may be shifted to a visible wavelength for display, preferably using a color that is prominent when superimposed on the visible light tissue image 402. The images 402, 404 may be frame-rate adjusted as appropriate for video display of the surgical field.

The images may be displayed separately as the visible light tissue image 402 and the near-infrared image 404. Or the images 402, 404 may be combined into a combined image 406 by the image processing unit described above. The combined image 406 may then be used as an aid to the procedures described above, or to any other surgical or diagnostic procedure that might benefit from the dye-based imaging techniques described herein.

It will be appreciated that the above functionality is merely illustrative, and that other dyes, imaging hardware, and optics may be usefully deployed with the imaging systems described herein. For example, an endoscopic tool may employ a still-image imaging system for diagnostic photography within a body cavity. Or any of the imaging systems may be used as described above with excitation and/or emission wavelengths in the far-red spectrum. Through minor adaptations that would be clear to one of ordinary skill in the art, the system could be configured to image two or more functions (i.e., tumor and blood flow) at the same time that a visible light image is captured by associating each function with a different dye having a different emission wavelength. Non-medical applications exist for the imaging system. For example, dyes in a solution form may be sprayed on a mechanical component to identify oxidation, surface defects, or the like. Dyes could also be used to track gas, steam, or air flow through a pressurized system, and in particular to identify leaks around fittings and valves. These and other arrangements and adaptations of the subject matter discussed herein are intended to fall within the scope of the invention. By way of example, a multi-channel imaging system applying the principles above is now described in greater detail.

In general, a medical imaging system may include a visible light source providing light over a range of wavelengths that includes one or more wavelengths of visible light, and an excitation light source providing light at one or more wavelengths outside the range of wavelengths of the visible light source. The one or more wavelengths are selected to excite one or more fluorescent substances, which emit fluorescence photons at different emission wavelengths. The system further includes an electronic imaging device, an optical guide that couples the image to the electronic image capture device, such as NIR and visible-light color cameras, and at least two dichroic mirrors or filters for separating the visible light from the two or more NIR wavelengths in the optical path of the system.

Figure 5:
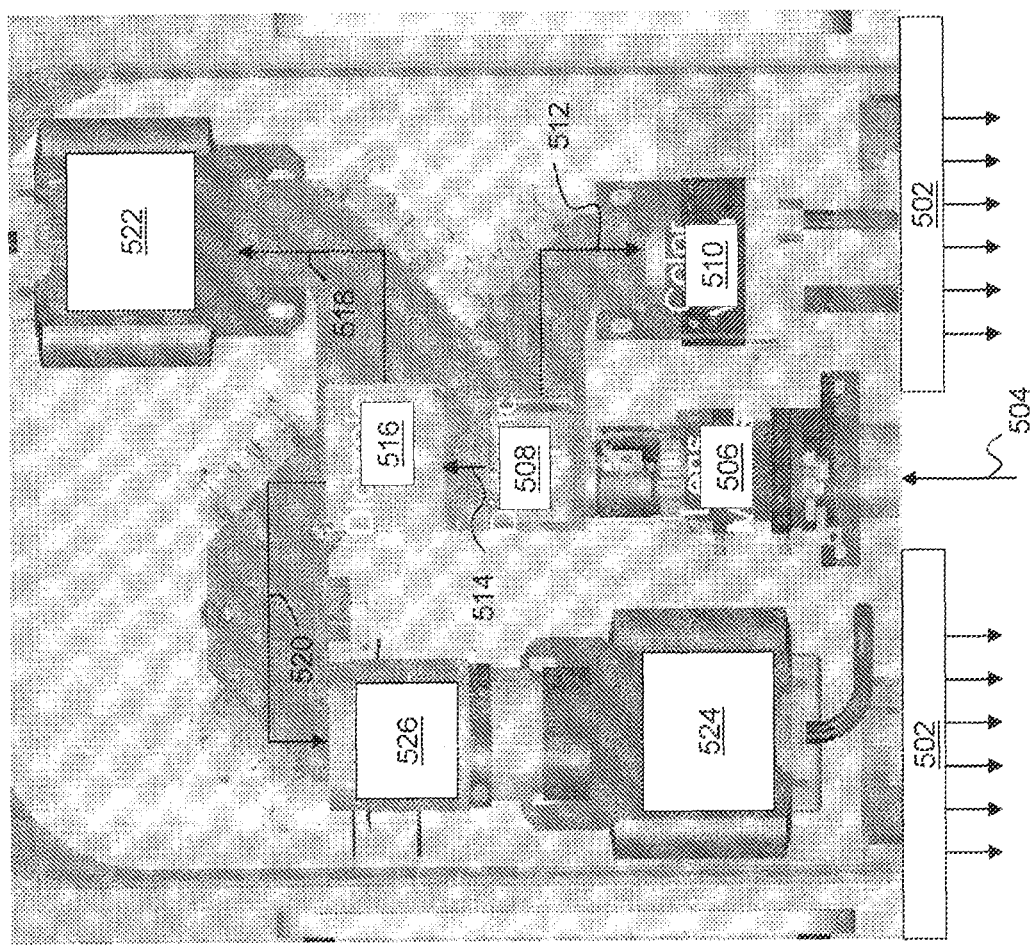
FIG. 5 schematically illustrates a dual-channel intraoperativee NIR fluorescence imaging system according to the invention.

FIG. 5 shows an embodiment of an imaging system 500 for visible and NIR light detection. The imaging system 500 may be, for example, a microscope, video system, or any other imaging system suitable for imaging medical subjects such as those described herein.

The imaging system may include a light source 502 including a visible light source and one or more different wavelength excitation light sources, which in the described exemplary embodiment are implemented as high-power white, NIR 1, and NIR 2 light-emitting diodes (LEDs). In general, a variety of techniques may be employed to obtain light of a desired wavelength or range of wavelengths from light emitting diodes. This may include, for example, filtering, mixing, wavelength shifting (such as with phosphors or the like), and so forth. Any suitable techniques for obtaining LED output of the desired wavelengths and sufficient intensity, or more generally for obtaining illumination of the desired wavelengths and sufficient intensity, may be employed with the systems described herein. In one embodiment, the light source 502 may include white LEDs conditioned to output light between 400 and 650 nm, NIR 1 LEDs conditioned to output light at 670 nm, and NIR 2 LEDs conditioned to output light at 760 nm. It will be understood that while specified as discrete wavelengths, LED and other light sources typically provide a range of wavelengths, and the specific wavelengths referred to herein are intended to describe light sources having a peak output at or substantially near the specified wavelength (or range of wavelengths). Additionally, a cooling plate or other active or passive heat dissipation system may be incorporated into the light source 502 to prevent or reduce overheating of the various light source elements. The system also includes an optional cooling stage for cooling a sample (not shown) positioned on a microscope stage or the like. The light source(s) 502 may be directed, focused, diffused, or conditioned using appropriate filters, lenses, and the like to illuminate a subject with desired light.

The system may also include a return optical path 504 along with focusing optics 506 such as a lens and other optics (zoom, focus, autofocus, pan, aperture, etc.) that may be controlled automatically or manually to obtain images from the subject.

A first dichroic mirror 508 (also referred to herein as a filter) may reflect visible light toward a video camera 510, such as a color video camera, as indicated by an arrow 512. The first dichroic mirror 508 may also transmit or pass light corresponding to the two diagnostic image wavelengths as indicated by an arrow 514. These excitation wavelengths, referred to herein as EXC 1 and EXC 2, corresponding to NIR 1 and NIR 2 respectively, may be any suitable wavelengths transmitted by the first dichroic mirror 508, such as substantially 700 nm and substantially 800 nm respectively.

A second dichroic mirror 516 may separate the excitation wavelengths into a first path for EXC 1, as indicated by a first arrow 518, and a second path for EXC 2 as indicated by a second arrow 520.

A first NIR camera 522, which may be a camera sensitive to approximately 700 nm, may receive the EXC 1 image on the first path 518. An image intensifier and/or other optics may be employed to focus, intensify, filter, or otherwise process the EXC 1 image. For example, a fitter may be employed to remove or reduce light above and/or below the EXC 1 wavelength, such as a filter that passes 689-725 nm. As another example, zoom or focus adjustment may be applied to compensate for reflected image shifts caused by the sputtering processes used to manufacture certain dichroic mirrors.

A second NIR camera 524, which may be a camera sensitive to approximately 800 nm, may receive the EXC 2 image on the second path 520. An image intensifier 526 and/or other optics may be employed to focus, intensify, filter, or otherwise process the EXC 2 image. The image intensifier 526 may be particularly suitable addition for the second NIR camera 524 in order to compensate for decreasing sensitivity of CCD imaging hardware at longer wavelengths. As another example, a filter may be employed to remove or reduce light above and/or below the EXC 2 wavelength, such as a filter that passes 800-948 nm. As another example, zoom or focus adjustment may be applied to compensate for reflected image shifts caused by the sputtering processes used to manufacture certain dichroic mirrors.

The system 500 may be employed, along with suitable computer hardware and software, to provide real-time overlay of anatomy and two different functional images. The system 500 provides a number of advantages. The lighting and imaging systems may be operated substantially continuously at conventional video rates without switched lighting, offset image sampling, or other complex hardware. This also mitigates thermal dissipation problems associated with high-power, high-speed switching that might otherwise be required. The system provides sufficient sensitivity to the NIR 1/EXC 1 and NIR 2/EXC 2 optical paths to operate in an area exposed to ambient light. Thus, in one aspect an imaging system for use in open surgical procedures is disclosed herein. The techniques described herein may also be adapted for use in endoscopic, laparoscopic, or other systems that offer a surgical field closed to ambient light, where multiple diagnostic image channels may also usefully be employed.

In one aspect, the visible light image, the first diagnostic image, and the second diagnostic image captured by the system 500 may be superimposed (in various combinations) tbr display as a surgical tool, diagnostic aid, and so forth. In general, each one of the first diagnostic image and the second diagnostic image may identify different regions of interest using dyes targeted for tumors, clots, or any other condition, tissue type, or the like.

In one aspect, circulation may be imaged using a dye in small-molecule form in a first optical channel, while a tumor or other region of interest may be imaged concurrently using a second dye containing a moiety for preferential uptake at the region of interest. A number of techniques are known for targeting dyes, including combination with moieties having affinity for chemicals, compounds, tissue, and so forth, or components that sequester or have preferential uptake at regions or items of interest. All such techniques suitable for use with the dyes described herein may be suitable employed as one of the two or more diagnostic image channels described herein. Using such techniques, diagnostic images may be usefully obtained for cranial nerves, peripheral nerves, bile ducts, ureters, thoracic duct, and any other anatomical structures. Dyes may also be targeted to clots, lesions, tumors, pre-cancerous cells, and so forth. It will be understood that showing or displaying a diagnostic image of an item (e.g., cranial nerves), as described herein is not intended to refer to incidental display of subject matter within a field of view. Rather, showing a diagnostic image as described herein generally refers to capturing a fluorescent image targeted to the region of interest by a fluorescent dye, and conversion to a readily visible pseudo-color (e.g., lime green or bright yellow) that can be superimposed on a visible light image.

Figure 6:
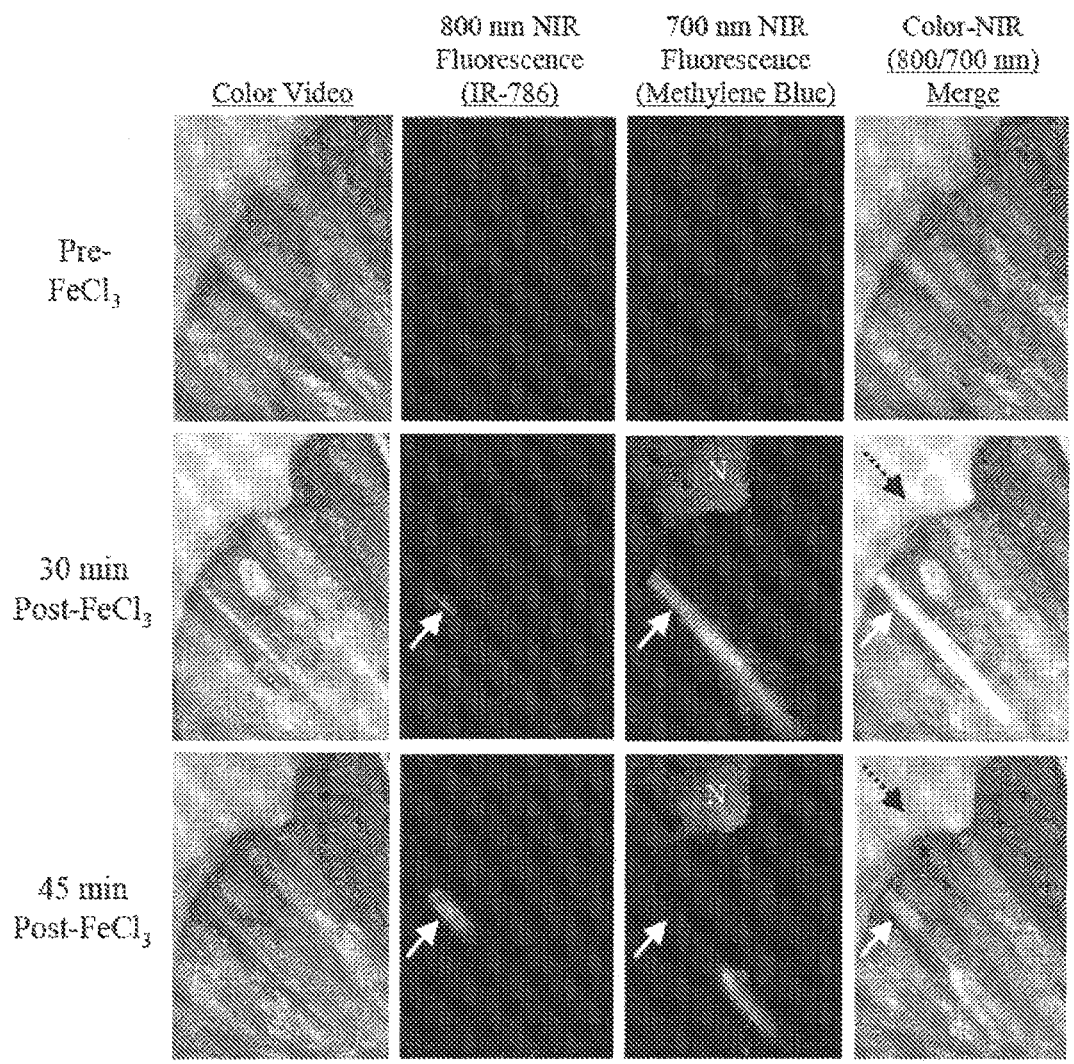
FIG. 6 shows a dual-channel NIR fluorescence image.

FIG. 6 shows dual-channel NIR fluorescence images 600 using NIR fluorescent platelets in 35 kilogram pigs. As discussed above, the intraoperative NIR fluorescence imaging system of FIG. 5 can be used to independently label any two targets. In this example, two bioactive NIR fluorescent platelets (800 nm fluorescence) and a 700 nm blood pool agent permit the real-time assessment of FeCl3-induced injury to the femoral artery. More specifically for this example, IR-786 may be employed to label platelets to fluoresce at 800 nm. Methylene blue may be employed to label blood to fluoresce at 700 nm. In this manner, blood flow is available as a 700 nm diagnostic (or EXC 1) image and platelet accumulation is available as an 800 am diagnostic (or EXC 2) image. In this example, intravascular thrombus is visualized with the 700 nm diagnostic image, which is indicated by white arrows and may be displayed using a first pseudo-color such as green. Blood flow is visualized with the 800 nm diagnostic image, which may be displayed using a second pseudo-color, such as yellow. The dotted black arrows in the right-hand side of FIG. 6 show the direction of blood flow. Note the increased autofluorescence of the nipple (N) in the 700 nm channel. Dual channel NIR fluorescence reveals vascular occlusion at 45 min post-FeCl3, leading to backfill from only collateral flow and an area of stagnation distal to the thrombus. Data are representative of 3 animals. While a number of suitable dyes for multi-channel imaging are described above, experimentally useful dyes for a multi-channel system include IRDye78 and IRDye800CW.

The images may be displayed separately as the visible light tissue image (left-hand column) and the two near-infrared images (second and third column from left). Alternatively, the two NIR 1 and NIR 2 images may be combined into a combined image (right-hand column) through suitable image processing. The separate or combined images may be used as an aid to surgical or diagnostic procedures that might benefit from the dye-based imaging techniques described herein.

It will be appreciated that the above functionality is merely illustrative, and that other dyes, imaging hardware, and optics may be usefully deployed with the imaging systems described herein. For example, excitation and/or emission wavelengths may be in the far-red spectrum. Through adaptations of the dichroic mirrors and/or filter optical paths, e.g., by positioning three or more dichroic mirrors (also referred to herein as filters) in the optical path, the system can image more than two functions tumor and blood flow) at the same time that a visible light image is captured by associating each function with a different dye having a different emission wavelength. These and other arrangements and adaptations of the subject matter discussed herein are intended to fall within the scope of the invention.

It should also be understood that all matter contained in the above description or shown in the accompanying drawings shall be interpreted as illustrative, and not in a limiting sense. Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

What is claimed is:

1. A system comprising:
   a light source providing visible light, a first excitation wavelength and a second excitation wavelength, the light source adapted to illuminate a subject; a lens that captures light from the subject;
   a first dichroic mirror that reflects visible light from the light toward a visible light camera as a visible light image and transmits wavelengths above a visible light range toward a second dichroic mirror;
   the second dichroic mirror reflecting a diagnostic image having a first wavelength toward a camera response to the first wavelength, and the second dichroic mirror transmitting a second diagnostic image having a second wavelength toward a camera responsive to the second wavelength; and
   a display that renders two or more of the visible light image, the diagnostic image, and the second diagnostic image superimposed on one another.

2. The system of claim 1 wherein the diagnostic image is a blood flow image.

3. The system of claim 1 wherein the diagnostic image includes a tumor.

4. The system of claim 1 wherein the first wavelength is a near-infrared wavelength.

5. The system of claim 1 wherein the first wavelength is substantially 700 nm and the second wavelength is substantially 800 nm.

6. The system of claim 1 wherein the light source includes a plurality of high-power light emitting diodes.

* * * * *